(12) United States Patent
Garcia-Echeverria et al.

(10) Patent No.: US 9,370,508 B2
(45) Date of Patent: Jun. 21, 2016

(54) IMIDAZOQUINOLINES AS DUAL LIPID KINASE AND MTOR INHIBITORS

(75) Inventors: Carlos Garcia-Echeverria, Basel (CH); Paul Leslie Nicklin, Horsham (GB); Leon Murphy, Brookline, MA (US); Sauveur-Michel Maira, Habsheim (FR); Peter Finan, Marblehead, MA (US); Christine Fritsch, Ranspach-le-Bas (FR); Saskia Maria Brachmann, Basel (CH)

(73) Assignee: NOVARTIS AG, Basel (CH)

( * ) Notice: Subject to any disclaimer, the term of this patent is extended or adjusted under 35 U.S.C. 154(b) by 90 days.

(21) Appl. No.: 12/525,333

(22) PCT Filed: Feb. 19, 2008

(86) PCT No.: PCT/US2008/054236
§ 371 (c)(1),
(2), (4) Date: Jul. 31, 2009

(87) PCT Pub. No.: WO2008/103636
PCT Pub. Date: Aug. 28, 2008

(65) Prior Publication Data
US 2010/0105696 A1 Apr. 29, 2010

Related U.S. Application Data

(60) Provisional application No. 60/890,641, filed on Feb. 20, 2007.

(51) Int. Cl.
*A61K 31/4745* (2006.01)

(52) U.S. Cl.
CPC .................................. *A61K 31/4745* (2013.01)

(58) Field of Classification Search
None
See application file for complete search history.

(56) References Cited

U.S. PATENT DOCUMENTS

| | | | |
|---|---|---|---|
| 2006/0199804 A1* | 9/2006 | Hummersone et al. | 514/218 |
| 2007/0032487 A1* | 2/2007 | Bruce et al. | 514/235.2 |
| 2008/0039459 A1* | 2/2008 | Folkes et al. | 514/234.2 |

FOREIGN PATENT DOCUMENTS

| | | |
|---|---|---|
| WO | 03/097641 | 11/2003 |
| WO | 2005/054237 | 6/2005 |
| WO | 2006/114606 A1 | 11/2006 |
| WO | 2006/122806 | 11/2006 |
| WO | WO 2006/125805 | * 11/2006 |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Ihle et al., Mol Aspects Med, 31(2):135-144, 2010.*
Tamura et al., Anti-inflammatory & Anti-allergy agents in Medicinal Chemistry, 6: 47-60, 2007.*
Tsang et al., Drug discovery, 12 (3/4): 112-124, 2007.*
François et al. (Journal of Virology, 77(4): 2539-2549, 2003).*
Johannessen et al. (PNAS, 102(24): 8573-8678, 2005).*
Richardson et al. (Seminars in Cell & Developmental Biology 15, 2004, 147-159).*
Nicola et al. (J. Virol. Jul. 2004 vol. 78 No. 14 7508-7517).*
Baselga J. et al: "A first-in-human phase I study of BKM120, an oral pan-class I PI3K inhibitor, in patients (pts) with advanced solid tumors", ASCO Meeting Abstracts Jun. 14, 2010:3003, pp. 1-4.
Inoki Ken et al: "Dysregulation of the TSC-mTOR pathway in human disease", Nature Genetics Jan. 2005, vol. 37, No. 1, Jan. 2005, pp. 19-24.
Hennessy, et al, "Exploiting the PI3K/AKT Pathway for Cancer Drug Discovery", Nature, Dec. 2005, vol. 4, pp. 988-1004.
Sabatini, "mTOR and Cancer : Insights into a Complex Relationship", Nature Reviews, vol. 6, Sep. 2006, pp. 729-734.
Young, et al, "mTOR—Beyond Transplantation", Science Direct, 2005, pp. 418-423.
Fan et al, "A dual PI3 kinase/mTOR inhibitor reveals emergent efficacy in glioma", Cancer Cell, May 2006, pp. 341-349.
Teachey et al, "The mTOR inhibitor CCI-779 induces apoptosis and inhibits growth in preclinical models of primary adult human ALL", Blood, 2006 107, pp. 1149-1155.
N. L. Glinka: General Chemistry, 27th stereotype edition, "Khimiya", Leningrad, Leningrad Department 1988, p. 453.
Pharmaceutics, vol. 2, under the editorship of L.A. Ivanova, Moscow "Meditisina" 1991, p. 21.
V.G. Belikov: Pharmaceutical Chemistry in two parts, second edition, "Vysshaya Shkola", Moscow, 1993, p. 43-47.
Bendell, et al. Phase I, Dose-Escalation Study of BKM120, an Oral Pan-Class I PI3K Inhibitor, in Patients with Advanced Solid Tumors. J. Clin. Oncol. 30(3): 282-290 (2012).
mTOR pathway 2009. Unknown author. (2008).

* cited by examiner

*Primary Examiner* — Bong-Sook Baek
(74) *Attorney, Agent, or Firm* — Qian Zhang

(57) ABSTRACT

The invention relates to the use of compounds of formula (I)

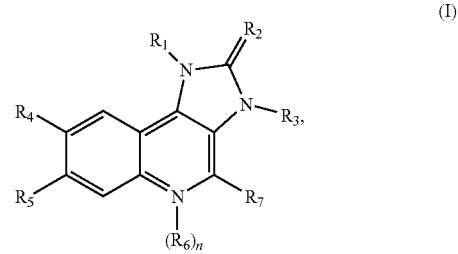

in the treatment of mammalian target of rapamycin (mTOR) kinase dependent diseases, methods of use of said compounds in the treatment of said diseases in a warm-blooded animal, especially a human, pharmaceutical preparations comprising said compounds for the treatment of said diseases and said compounds for use in the treatment of said diseases.

1 Claim, No Drawings

IMIDAZOQUINOLINES AS DUAL LIPID KINASE AND MTOR INHIBITORS

This is a National Stage of International Application No. PCT/US2008/054236 filed 19 Feb. 2008, which claims benefit of U.S. Provisional Application No. 60/890,641 filed 20 Feb. 2007, which in its entirety are herein incorporated by reference.

The present invention relates to the use of specific imidazoquinoline derivatives in the treatment of mammalian target of rapamycin (mTOR) kinase dependent diseases or for the manufacture of pharmaceutical compositions for use in the treatment of said diseases, methods of use of specific imidazoquinolines in the treatment of said diseases in a warm-blooded animal, especially a human, pharmaceutical preparations comprising specific imidazoquinolines for the treatment of said diseases and specific imidazoquinolines for use in the treatment of said diseases.

Surprisingly, it has been found that specific imidazoquinoline derivatives, which have been described in WO2006/122806 to inhibit the activity of lipid kinases, such as PI3-kinases, do also inhibit mTOR Ser/Thr kinase activity. Said compounds are therefore dual PI3-kinase and mTOR inhibitors and thus are useful for the treatment of such mTOR kinase dependent diseases.

Syndromes with an established or potential molecular link to dysregulation of mTOR kinase activity are, for instance, described in "K. Inoki et al.; Dysregulation of the TSC-mTOR pathway in human disease, Nature Genetics, vol 37, 19-24"; "D. M. Sabatini; mTOR and cancer: insights into a complex relationship, Nature Reviews, vol. 6, 729-734"; and in "B. T. Hennessy et al.; Exploiting the PI3K/Akt pathway for cancer drug discovery, Nature Reviews, vol. 4, 988-1004", which all are, including the references cited therein, hereby incorporated into the present application by reference, and are as follows:

Organ or tissue transplant rejection, e.g. for the treatment of recipients of e.g. heart, lung, combined heart-lung, liver, kidney, pancreatic, skin or corneal transplants; graft-versus-host disease, such as following bone marrow transplantation;
Restenosis
Tuberous sclerosis
Lymphangioleiomyomatosis
Retinitis pigmentosis
Autoimmune diseases including encephalomyelitis, insulin-dependent diabetes mellitus, lupus, dermatomyositis, arthritis and rheumatic diseases
Steroid-resistant acute Lymphoblastic Leukaemia
Fibrotic diseases including scleroderma, pulmonary fibrosis, renal fibrosis, cystic fibrosis
Pulmonary hypertension
Immunomodulation
Multiple sclerosis
VHL syndrome
Carney complex
Familial adenonamtous polyposis
Juvenile polyposis syndrome
Birt-Hogg-Duke syndrome
Familial hypertrophic cardiomyopathy
Wolf-Parkinson-White syndrome
Neurodegenerative disorders such as Parkinson's, Huntington's, Alzheimer's and dementias caused by tau mutations, spinocerebellar ataxia type 3, motor neuron disease caused by SOD1 mutations, neuronal ceroid lipofucinoses/Batten disease (pediatric neurodegeneration)
wet and dry macular degeneration
muscle wasting (atrophy, cachexia) and myopathies such as Danon's disease.
bacterial and viral infections including *M. tuberculosis*, group A *streptococcus*, HSV type I, HIV infection
Neurofibromatosis including Neurofibromatosis type 1, Peutz-Jeghers syndrome
or further any combinations thereof.

The efficacy of a dual PI3 kinase/mTOR inhibitor in malignant glioma has been recently described (Cancer Cell 9, 341-349).

Specific imidazoquinoline derivatives which are suitable for the present invention, their preparation and suitable pharmaceutical formulations containing the same are described in WO2006/122806 and include compounds of formula I

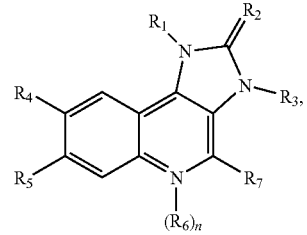

wherein
$R_1$ is naphthyl or phenyl wherein said phenyl is substituted by one or two substituents independently selected from the group consisting of Halogen; lower alkyl unsubstituted or substituted by halogen, cyano, imidazolyl or triazolyl; cycloalkyl; amino substituted by one or two substituents independently selected from the group consisting of lower alkyl, lower alkyl sulfonyl, lower alkoxy and lower alkoxy lower alkylamino; piperazinyl unsubstituted or substituted by one or two substituents independently selected from the group consisting of lower alkyl and lower alkyl sulfonyl; 2-oxo-pyrrolidinyl; lower alkoxy lower alkyl; imidazolyl; pyrazolyl; and triazolyl;
$R_2$ is O or S;
$R_3$ is lower alkyl;
$R_4$ is pyridyl unsubstituted or substituted by halogen, cyano, lower alkyl, lower alkoxy or piperazinyl unsubstituted or substituted by lower alkyl; pyrimidinyl unsubstituted or substituted by lower alkoxy; quinolinyl unsubstituted or substituted by halogen; quinoxalinyl; or phenyl substituted with alkoxy
$R_5$ is hydrogen or halogen;
n is 0 or 1;
$R_6$ is oxido;
with the proviso that if n=1, the N-atom bearing the radical $R_6$ has a positive charge;
$R_7$ is hydrogen or amino;
or a tautomer thereof, or a pharmaceutically acceptable salt, or a hydrate or solvate thereof.

The radicals and symbols used in the definition of a compound of formula I have the meanings disclosed in U.S. Pat. Pub. 2008/0194579 A1 (corresponding to WO2006/122806) which publication is hereby incorporated into the present application by reference.

A preferred compound of the present invention is a compound—described in WO2006/122806—chosen from the group consisting of;
2-Methyl-2-[4-(3-methyl-2-oxo-8-pyridin-4-yl-2,3-dihydro-imidazo[4,5-c]quinolin-1-yl)-phenyl]-propionitrile;

2-Methyl-2-[4-(3-methyl-2-oxo-8-pyridin-3-yl-2,3-dihydro-imidazo[4,5-c]quinolin-1-yl)-phenyl]-propionitrile;
2-{-4-[8-(6-Methoxy-pyridin-3-yl)-3-methyl-2-oxo-2,3-dihydro-imidazo[4,5-c]quinolin-1-yl]-phenyl}-2-methyl-propionitrile;
2-{-4-[8-(5-Methoxy-pyridin-3-yl)-3-methyl-2-oxo-2,3-dihydro-imidazo[4,5-c]quinolin-1-yl]-phenyl}-2-methyl-propionitrile;
2-Methyl-2-{-4-[3-methyl-2-oxo-8-(6-piperazin-1-yl-pyridin-3-yl)-2,3-dihydro-imidazo[4,5-c]quinolin-1-yl]-phenyl}-propionitrile;
2-Methyl-2-(4-{3-methyl-8-[2-(4-methyl-piperazin-1-yl)-pyridin-4-yl]-2-oxo-2,3-dihydro-imidazo[4,5-c]quinolin-1-yl}-phenyl)-propionitrile;
2-Methyl-2-[4-(3-methyl-2-oxo-8-quinolin-3-yl-2,3-dihydro-imidazo[4,5-c]quinolin-1-yl)-phenyl]-propionitrile;
2-{-4-[8-(2-Fluoro-quinolin-3-yl)-3-methyl-2-oxo-2,3-dihydro-imidazo[4,5-c]quinolin-1-yl]-phenyl}-2-methyl-propionitrile;
2-Methyl-2-[4-(3-methyl-2-oxo-8-quinolin-6-yl-2,3-dihydro-imidazo[4,5-c]quinolin-1-yl)-phenyl]-propionitrile;
2-Methyl-2-[4-(3-methyl-2-oxo-8-quinolin-5-yl-2,3-dihydro-imidazo[4,5-c]quinolin-1-yl)-phenyl]-propionitrile;
2-Methyl-2-[4-(3-methyl-2-oxo-8-quinoxalin-6-yl-2,3-dihydro-imidazo[4,5-c]quinolin-1-yl)-phenyl]-propionitrile;
2-Ethyl-2-[4-(3-methyl-2-oxo-8-pyridin-3-yl-2,3-dihydro-imidazo[4,5-c]quinolin-1-yl)-phenyl]-butyronitrile;
2-Ethyl-2-[4-(3-methyl-2-oxo-8-quinolin-3-yl-2,3-dihydro-imidazo[4,5-c]quinolin-1-yl)-phenyl]-butyronitrile;
1-[3-Fluoro-4-(2-oxo-pyrrolidin-1-yl)-phenyl]-3-methyl-8-pyridin-3-yl-1,3-dihydro-imidazo[4,5-c]quinolin-2-one;
1-[3-Fluoro-4-(2-oxo-pyrrolidin-1-yl)-phenyl]-3-methyl-8-quinolin-3-yl-1,3-dihydro-imidazo[4,5-c]quinolin-2-one;
3-Methyl-1-[4-(2-oxo-pyrrolidin-1-yl)-phenyl]-8-pyridin-3-yl-1,3-dihydro-imidazo[4,5-c]quinolin-2-one;
3-Methyl-1-[4-(2-oxo-pyrrolidin-1-yl)-phenyl]-8-quinolin-3-yl-1,3-dihydro-imidazo[4,5-c]quinolin-2-one;
1-{4-[Bis-(2-methoxy-ethyl)-amino]-3-fluoro-phenyl}-3-methyl-8-pyridin-3-yl-1,3-dihydro-imidazo[4,5-c]quinolin-2-one;
1-{4-[Bis-(2-methoxy-ethyl)-amino]-3-fluoro-phenyl}-3-methyl-8-quinolin-3-yl-1,3-dihydro-imidazo[4,5-c]quinolin-2-one;
1-{4-[Bis-(2-methoxy-ethyl)-amino]-phenyl}-3-methyl-8-pyridin-3-yl-1,3-dihydro-imidazo[4,5-c]quinolin-2-one;
1-{4-[Bis-(2-methoxy-ethyl)-amino]-phenyl}-3-methyl-8-quinolin-3-yl-1,3-dihydro-imidazo[4,5-c]quinolin-2-one;
3-Methyl-1-naphthalen-2-yl-8-pyridin-3-yl-1,3-dihydro-imidazo[4,5-c]quinolin-2-one;
3-Methyl-1-naphthalen-2-yl-8-quinolin-3-yl-1,3-dihydro-imidazo[4,5-c]quinolin-2-one;
1-(2-Chloro-phenyl)-3-methyl-8-pyridin-3-yl-1,3-dihydro-imidazo[4,5-c]quinolin-2-one;
1-(2-Chloro-phenyl)-3-methyl-8-quinolin-3-yl-1,3-dihydro-imidazo[4,5-c]quinolin-2-one;
3-Methyl-8-pyridin-3-yl-1-o-tolyl-1,3-dihydro-imidazo[4,5-c]quinolin-2-one;
3-Methyl-8-quinolin-3-yl-1-o-tolyl-1,3-dihydro-imidazo[4,5-c]quinolin-2-one;
1-(2-Ethyl-phenyl)-3-methyl-8-pyridin-3-yl-1,3-dihydro-imidazo[4,5-c]quinolin-2-one;
1-(2-Ethyl-phenyl)-3-methyl-8-quinolin-3-yl-1,3-dihydro-imidazo[4,5-c]quinolin-2-one;
3-Methyl-8-pyridin-3-yl-1-(2-trifluoromethyl-phenyl)-1,3-dihydro-imidazo[4,5-c]quinolin-2-one;
3-Methyl-8-quinolin-3-yl-1-(2-trifluoromethyl-phenyl)-1,3-dihydro-imidazo[4,5-c]quinolin-2-one;
1-(4-Fluoro-2-methyl-phenyl)-3-methyl-8-quinolin-3-yl-1,3-dihydro-imidazo[4,5-c]quinolin-2-one;
1-(4-Fluoro-2-methyl-phenyl)-3-methyl-8-quinolin-3-yl-1,3-dihydro-imidazo[4,5-c]quinolin-2-one;
1-(2-Chloro-4-fluoro-phenyl)-3-methyl-8-pyridin-3-yl-1,3-dihydro-imidazo[4,5-c]quinolin-2-one;
1-(2-Chloro-4-fluoro-phenyl)-3-methyl-8-quinolin-3-yl-1,3-dihydro-imidazo[4,5-c]quinolin-2-one;
1-(3-Chloro-phenyl)-3-methyl-8-pyridin-3-yl-1,3-dihydro-imidazo[4,5-c]quinolin-2-one;
1-(3-Chloro-phenyl)-3-methyl-8-quinolin-3-yl-1,3-dihydro-imidazo[4,5-c]quinolin-2-one;
3-Methyl-8-pyridin-3-yl-1-(3-trifluoromethyl-phenyl)-1,3-dihydro-imidazo[4,5-c]quinolin-2-one;
3-Methyl-8-quinolin-3-yl-1-(3-trifluoromethyl-phenyl)-1,3-dihydro-imidazo[4,5-c]quinolin-2-one;
1-(4-Methoxymethyl-phenyl)-3-methyl-8-pyridin-3-yl-1,3-dihydro-imidazo[4,5-c]quinolin-2-one;
1-(4-Methoxymethyl-phenyl)-3-methyl-8-quinolin-3-yl-1,3-dihydro-imidazo[4,5-c]quinolin-2-one;
1-[2-Chloro-4-(2-methoxy-ethyl)-phenyl]-3-methyl-8-pyridin-3-yl-1,3-dihydro-imidazo[4,5-c]quinolin-2-one;
1-[2-Chloro-4-(2-methoxy-ethyl)-phenyl]-3-methyl-8-quinolin-3-yl-1,3-dihydro-imidazo[4,5-c]quinolin-2-one;
1-[4-(2-Methoxy-ethyl)-phenyl]-3-methyl-8-quinolin-3-yl-1,3-dihydro-imidazo[4,5-c]quinolin-2-one;
1-[4-(2-Methoxy-ethyl)-phenyl]-3-methyl-8-pyridin-3-yl-1,3-dihydro-imidazo[4,5-c]quinolin-2-one;
2-Methyl-2-[4-(3-methyl-2-oxo-5-oxy-8-pyridin-3-yl-2,3-dihydro-imidazo[4,5-c]quinolin-1-yl)-phenyl]-propionitrile;
2-Methyl-2-[4-(3-methyl-2-oxo-5-oxy-8-quinolin-3-yl-2,3-dihydro-imidazo[4,5-c]quinolin-1-yl)-phenyl]-propionitrile;
2-[4-(7-Fluoro-3-methyl-2-oxo-8-pyridin-3-yl-2,3-dihydro-imidazo[4,5-c]quinolin-1-yl)-phenyl]-2-methyl-propionitrile;
2-[4-(7-Fluoro-3-methyl-2-oxo-8-quinolin-3-yl-2,3-dihydro-imidazo[4,5-c]quinolin-1-yl)-phenyl]-2-methyl-propionitrile;
N-Methyl-N-[4-(3-methyl-2-oxo-8-pyridin-3-yl-2,3-dihydro-imidazo[4,5-c]quinolin-1-yl)-phenyl]-methanesulfonamide;
Methyl-[4-(3-methyl-2-oxo-8-pyridin-3-yl-2,3-dihydro-imidazo[4,5-c]quinolin-1-yl)-phenyl]-carbamic acid tert-butyl ester;
Ethanesulfonic acid methyl-[4-(3-methyl-2-oxo-8-pyridin-3-yl-2,3-dihydro-imidazo[4,5-c]quinolin-1-yl)-phenyl]-amide;
Ethanesulfonic acid methyl-[4-(3-methyl-2-oxo-8-quinolin-3-yl-2,3-dihydro-imidazo[4,5-c]quinolin-1-yl)-phenyl]-amide;
N-Ethyl-N-[4-(3-methyl-2-oxo-8-pyridin-3-yl-2,3-dihydro-imidazo[4,5-c]quinolin-1-yl)-phenyl]-methanesulfonamide;
N-Ethyl-N-[4-(3-methyl-2-oxo-8-quinolin-3-yl-2,3-dihydro-imidazo[4,5-c]quinolin-1-yl)-phenyl]-methanesulfonamide;
2-[4-(3-Ethyl-2-oxo-8-pyridin-3-yl-2,3-dihydro-imidazo[4,5-c]quinolin-1-yl)-phenyl]-2-methyl-propionitrile;
1-[3-Fluoro-4-(4-methanesulfonyl-piperazin-1-yl)-phenyl]-3-methyl-8-quinolin-3-yl-1,3-dihydro-imidazo[4,5-c]quinolin-2-one;

1-[3-Fluoro-4-(4-methanesulfonyl-piperazin-1-yl)-phenyl]-3-methyl-8-pyridin-3-yl-1,3-dihydro-imidazo[4,5-c]quinolin-2-one;

1-(3-Fluoro-4-piperazin-1-yl-phenyl)-3-methyl-8-quinolin-3-yl-1,3-dihydro-imidazo[4,5-c]quinolin-2-one;

1-(3-Fluoro-4-piperazin-1-yl-phenyl)-3-methyl-8-pyridin-3-yl-1,3-dihydro-imidazo[4,5-c]quinolin-2-one;

3-Methyl-1-[4-(4-methyl-piperazin-1-yl)-phenyl]-8-quinolin-3-yl-1,3-dihydro-imidazo[4,5-c]quinolin-2-one;

3-Methyl-1-[4-(4-methyl-piperazin-1-yl)-phenyl]-8-pyridin-3-yl-1,3-dihydro-imidazo[4,5-c]quinolin-2-one;

1-[2-Chloro-4-(4-methyl-piperazin-1-yl)-phenyl]-3-methyl-8-quinolin-3-yl-1,3-dihydro-imidazo[4,5-c]quinolin-2-one;

1-[2-Chloro-4-(4-methyl-piperazin-1-yl)-phenyl]-3-methyl-8-pyridin-3-yl-1,3-dihydro-imidazo[4,5-c]quinolin-2-one;

1-[3-Chloro-4-(4-methyl-piperazin-1-yl)-phenyl]-3-methyl-8-quinolin-3-yl-1,3-dihydro-imidazo[4,5-c]quinolin-2-one;

1-[3-Chloro-4-(4-methyl-piperazin-1-yl)-phenyl]-3-methyl-8-pyridin-3-yl-1,3-dihydro-imidazo[4,5-c]quinolin-2-one;

1-(4-Imidazol-1-yl-2-methyl-phenyl)-3-methyl-8-quinolin-3-yl-1,3-dihydro-imidazo[4,5-c]quinolin-2-one;

1-(4-Imidazol-1-yl-2-methyl-phenyl)-3-methyl-8-pyridin-3-yl-1,3-dihydro-imidazo[4,5-c]quinolin-2-one;

3-Methyl-1-(4-pyrazol-1-yl-phenyl)-8-quinolin-3-yl-1,3-dihydro-imidazo[4,5-c]quinolin-2-one;

3-Methyl-1-(4-pyrazol-1-yl-phenyl)-8-pyridin-3-yl-1,3-dihydro-imidazo[4,5-c]quinolin-2-one;

3-Methyl-8-quinolin-3-yl-1-(4-[1,2,4]triazol-1-yl-phenyl)-1,3-dihydro-imidazo[4,5-c]quinolin-2-one;

3-Methyl-8-pyridin-3-yl-1-(4-[1,2,4]triazol-1-yl-phenyl)-1,3-dihydro-imidazo[4,5-c]quinolin-2-one;

3-Methyl-1-[4-(4-methyl-piperazin-1-yl)-3-trifluoromethyl-phenyl]-8-quinolin-3-yl-1,3-dihydro-imidazo[4,5-c]quinolin-2-one;

3-Methyl-1-[4-(4-methyl-piperazin-1-yl)-3-trifluoromethyl-phenyl]-8-pyridin-3-yl-1,3-dihydro-imidazo[4,5-c]quinolin-2-one;

1-(3-Chloro-4-piperazin-1-yl-phenyl)-3-methyl-8-quinolin-3-yl-1,3-dihydro-imidazo[4,5-c]quinolin-2-one;

1-(3-Chloro-4-piperazin-1-yl-phenyl)-3-methyl-8-pyridin-3-yl-1,3-dihydro-imidazo[4,5-c]quinolin-2-one;

1-(3-Chloro-4-piperazin-1-yl-phenyl)-8-(6-methoxy-pyridin-3-yl)-3-methyl-1,3-dihydro-imidazo[4,5-c]quinolin-2-one;

1-(3-Chloro-4-piperazin-1-yl-phenyl)-8-(5-methoxy-pyridin-3-yl)-3-methyl-1,3-dihydro-imidazo[4,5-c]quinolin-2-one;

8-(6-Methoxy-pyridin-3-yl)-3-methyl-1-[4-(4-methyl-piperazin-1-yl)-3-trifluoromethyl-phenyl]-1,3-dihydro-imidazo[4,5-c]quinolin-2-one;

8-(5-Methoxy-pyridin-3-yl)-3-methyl-1-[4-(4-methyl-piperazin-1-yl)-3-trifluoromethyl-phenyl]-1,3-dihydro-imidazo[4,5-c]quinolin-2-one;

1-[2-Chloro-4-(4-methyl-piperazin-1-yl)-phenyl]-8-(6-methoxy-pyridin-3-yl)-3-methyl-1,3-dihydro-imidazo[4,5-c]quinolin-2-one;

1-[2-Chloro-4-(4-methyl-piperazin-1-yl)-phenyl]-8-(5-methoxy-pyridin-3-yl)-3-methyl-1,3-dihydro-imidazo[4,5-c]quinolin-2-one;

1-(3-Chloro-4-piperazin-1-yl-phenyl)-3-methyl-8-quinoxalin-6-yl-1,3-dihydro-imidazo[4,5-c]quinolin-2-one;

3-Methyl-1-(4-piperazin-1-yl-3-trifluoromethyl-phenyl)-8-quinolin-3-yl-1,3-dihydro-imidazo[4,5-c]quinolin-2-one;

3-Methyl-1-(4-piperazin-1-yl-3-trifluoromethyl-phenyl)-8-pyridin-3-yl-1,3-dihydro-imidazo[4,5-c]quinolin-2-one;

8-(6-Methoxy-pyridin-3-yl)-3-methyl-1-(4-piperazin-1-yl-3-trifluoromethyl-phenyl)-1,3-dihydro-imidazo[4,5-c]quinolin-2-one;

8-(5-Methoxy-pyridin-3-yl)-3-methyl-1-(4-piperazin-1-yl-3-trifluoromethyl-phenyl)-1,3-dihydro-imidazo[4,5-c]quinolin-2-one;

3-Methyl-1-(4-piperazin-1-yl-3-trifluoromethyl-phenyl)-8-quinoxalin-6-yl-1,3-dihydro-imidazo[4,5-c]quinolin-2-one;

1-[3-Chloro-4-(cis-3,5-dimethyl-piperazin-1-yl)-phenyl]-3-methyl-8-pyridin-3-yl-1,3-dihydro-imidazo[4,5-c]quinolin-2-one;

1-[3-Chloro-4-(cis-3,5-dimethyl-piperazin-1-yl)-phenyl]-3-methyl-8-quinolin-3-yl-1,3-dihydro-imidazo[4,5-c]quinolin-2-one;

1-[3-Chloro-4-(4-ethyl-piperazin-1-yl)-phenyl]-3-methyl-8-pyridin-3-yl-1,3-dihydro-imidazo[4,5-c]quinolin-2-one;

1-[3-Chloro-4-(4-ethyl-piperazin-1-yl)-phenyl]-3-methyl-8-quinolin-3-yl-1,3-dihydro-imidazo[4,5-c]quinolin-2-one;

1-[3-Chloro-4-(4-isopropyl-piperazin-1-yl)-phenyl]-3-methyl-8-pyridin-3-yl-1,3-dihydro-imidazo[4,5-c]quinolin-2-one;

1-[3-Chloro-4-(4-isopropyl-piperazin-1-yl)-phenyl]-3-methyl-8-quinolin-3-yl-1,3-dihydro-imidazo[4,5-c]quinolin-2-one;

1-[3-Chloro-4-(4-isopropyl-piperazin-1-yl)-phenyl]-3-methyl-8-pyridin-3-yl-1,3-dihydro-imidazo[4,5-c]quinolin-2-one;

1-[3-Chloro-4-(4-isopropyl-piperazin-1-yl)-phenyl]-3-methyl-8-quinolin-3-yl-1,3-dihydro-imidazo[4,5-c]quinolin-2-one;

1-[4-(4-Ethyl-piperazin-1-yl)-3-trifluoromethyl-phenyl]-3-methyl-8-pyridin-3-yl-1,3-dihydro-imidazo[4,5-c]quinolin-2-one;

1-[4-(4-Ethyl-piperazin-1-yl)-3-trifluoromethyl-phenyl]-3-methyl-8-quinolin-3-yl-1,3-dihydro-imidazo[4,5-c]quinolin-2-one;

1-[4-(4-Ethyl-piperazin-1-yl)-3-trifluoromethyl-phenyl]-3-methyl-8-pyridin-3-yl-1,3-dihydro-imidazo[4,5-c]quinolin-2-one;

1-[4-(4-Ethyl-piperazin-1-yl)-3-trifluoromethyl-phenyl]-3-methyl-8-quinolin-3-yl-1,3-dihydro-imidazo[4,5-c]quinolin-2-one;

3-Methyl-8-(6-piperazin-1-yl-pyridin-3-yl)-1-(3-trifluoromethyl-phenyl)-1,3-dihydro-imidazo[4,5-c]quinolin-2-one;

8-(6-Methoxy-pyridin-3-yl)-3-methyl-1-(3-trifluoromethyl-phenyl)-1,3-dihydro-imidazo[4,5-c]quinolin-2-one;

8-(6-Methoxy-pyridin-3-yl)-3-methyl-1-(3-trifluoromethyl-phenyl)-1,3-dihydro-imidazo[4,5-c]quinolin-2-one;

1-(3-Chloro-4-imidazol-1-yl-phenyl)-3-methyl-8-pyridin-3-yl-1,3-dihydro-imidazo[4,5-c]quinolin-2-one;

1-(3-Chloro-4-imidazol-1-yl-phenyl)-3-methyl-8-quinolin-3-yl-1,3-dihydro-imidazo[4,5-c]quinolin-2-one;

2-Methyl-2-[4-(3-methyl-8-quinolin-3-yl-2-thioxo-2,3-dihydro-imidazo[4,5-c]quinolin-1-yl)-phenyl]-propionitrile;

2-Methyl-2-{-4-[3-methyl-8-(2-methyl-pyridin-4-yl)-2-oxo-2,3-dihydro-imidazo[4,5-c]quinolin-1-yl]-phenyl}-propionitrile;

5-{1-[4-(Cyano-dimethyl-methyl)-phenyl]-3-methyl-2-oxo-2,3-dihydro-1H-imidazo[4,5-c]quinolin-8-yl}-pyridine-2-carbonitrile;

2-[4-(4-Amino-3-methyl-2-oxo-8-quinolin-3-yl-2,3-dihydro-imidazo[4,5-c]quinolin-1-yl)-phenyl]-2-methyl-propionitrile;

1-[4-(3-Methyl-2-oxo-8-pyridin-3-yl-2,3-dihydro-imidazo[4,5-c]quinolin-1-yl)-phenyl]-cyclopropanecarbonitrile;
1-[4-(3-Methyl-2-oxo-8-quinolin-3-yl-2,3-dihydro-imidazo[4,5-c]quinolin-1-yl)-phenyl]-cyclopropanecarbonitrile;
1-{-4-[8-(6-Methoxy-pyridin-3-yl)-3-methyl-2-oxo-2,3-dihydro-imidazo[4,5-c]quinolin-1-yl]-phenyl}-cyclopropanecarbonitrile;
1-[3-Chloro-4-(4-methyl-piperazin-1-yl)-phenyl]-8-(6-methoxy-pyridin-3-yl)-3-methyl-1,3-dihydro-imidazo[4,5-c]quinolin-2-one;
1-[3-Chloro-4-(4-methyl-piperazin-1-yl)-phenyl]-8-(5-methoxy-pyridin-3-yl)-3-methyl-1,3-dihydro-imidazo[4,5-c]quinolin-2-one;
1-[3-Chloro-4-(4-methyl-piperazin-1-yl)-phenyl]-3-methyl-8-quinoxalin-6-yl-1,3-dihydro-imidazo[4,5-c]quinolin-2-one;
1-(3-Chloro-4-piperazin-1-yl-phenyl)-8-(2-methoxy-pyrimidin-5-yl)-3-methyl-1,3-dihydro-imidazo[4,5-c]quinolin-2-one;
1-(3-Chloro-4-piperazin-1-yl-phenyl)-3-methyl-8-pyrimidin-5-yl-1,3-dihydro-imidazo[4,5-c]quinolin-2-one;
1-(3-Chloro-4-piperazin-1-yl-phenyl)-8-(2-methoxy-pyrimidin-5-yl)-3-methyl-1,3-dihydro-imidazo[4,5-c]quinolin-2-one;
1-(3-Chloro-4-piperazin-1-yl-phenyl)-3-methyl-8-pyrimidin-5-yl-1,3-dihydro-imidazo[4,5-c]quinolin-2-one;
1-(3-Chloro-4-piperazin-1-yl-phenyl)-3-methyl-8-(2-methyl-pyridin-4-yl)-1,3-dihydro-imidazo[4,5-c]quinolin-2-one;
1-[3-Chloro-4-(cis-3,5-dimethyl-piperazin-1-yl)-phenyl]-8-(6-methoxy-pyridin-3-yl)-3-methyl-1,3-dihydro-imidazo[4,5-c]quinolin-2-one;
1-[3-Chloro-4-(cis-3,5-dimethyl-piperazin-1-yl)-phenyl]-8-(5-methoxy-pyridin-3-yl)-3-methyl-1,3-dihydro-imidazo[4,5-c]quinolin-2-one;
1-[4-(cis-3,5-Dimethyl-piperazin-1-yl)-3-trifluoromethyl-phenyl]-8-(6-methoxy-pyridin-3-yl)-3-methyl-1,3-dihydro-imidazo[4,5-c]quinolin-2-one;
1-[4-(cis-3,5-Dimethyl-piperazin-1-yl)-3-trifluoromethyl-phenyl]-8-(5-methoxy-pyridin-3-yl)-3-methyl-1,3-dihydro-imidazo[4,5-c]quinolin-2-one;
8-(2-Methoxy-pyrimidin-5-yl)-3-methyl-1-(4-piperazin-1-yl-3-trifluoromethyl-phenyl)-1,3-dihydro-imidazo[4,5-c]quinolin-2-one;
3-Methyl-1-(4-piperazin-1-yl-3-trifluoromethyl-phenyl)-8-pyrimidin-5-yl-1,3-dihydro-imidazo[4,5-c]quinolin-2-one;
5-[3-Methyl-2-oxo-1-(4-piperazin-1-yl-3-trifluoromethyl-phenyl)-2,3-dihydro-1H-imidazo[4,5-c]quinolin-8-yl]-pyridine-2-carbonitrile;
3-Methyl-8-(2-methyl-pyridin-4-yl)-1-(4-piperazin-1-yl-3-trifluoromethyl-phenyl)-1,3-dihydro-imidazo[4,5-c]quinolin-2-one;
8-(3,4-Dimethoxy-phenyl)-3-methyl-1-(4-piperazin-1-yl-3-trifluoromethyl-phenyl)-1,3-dihydro-imidazo[4,5-c]quinolin-2-one;
3-Methyl-8-pyridin-3-yl-1-(4-[1,2,4]triazol-1-yl-3-trifluoromethyl-phenyl)-1,3-dihydro-imidazo[4,5-c]quinolin-2-one;
3-Methyl-8-quinolin-3-yl-1-(4-[1,2,4]triazol-1-yl-3-trifluoromethyl-phenyl)-1,3-dihydro-imidazo[4,5-c]quinolin-2-one;
8-(6-Methoxy-pyridin-3-yl)-3-methyl-1-(4-[1,2,4]triazol-1-yl-3-trifluoromethyl-phenyl)-1,3-dihydro-imidazo[4,5-c]quinolin-2-one;
8-(5-Methoxy-pyridin-3-yl)-3-methyl-1-(4-[1,2,4]triazol-1-yl-3-trifluoromethyl-phenyl)-1,3-dihydro-imidazo[4,5-c]quinolin-2-one;
5-[3-Methyl-2-oxo-1-(4-[1,2,4]triazol-1-yl-3-trifluoromethyl-phenyl)-2,3-dihydro-1H-imidazo[4,5-c]quinolin-8-yl]-pyridine-2-carbonitrile;
8-(6-Fluoro-pyridin-3-yl)-3-methyl-1-(4-[1,2,4]triazol-1-yl-3-trifluoromethyl-phenyl)-1,3-dihydro-imidazo[4,5-c]quinolin-2-one;
8-(2,6-Dimethoxy-pyridin-3-yl)-3-methyl-1-(4-[1,2,4]triazol-1-yl-3-trifluoromethyl-phenyl)-1,3-dihydro-imidazo[4,5-c]quinolin-2-one;
3-Methyl-8-pyrimidin-5-yl-1-(4-[1,2,4]triazol-1-yl-3-trifluoromethyl-phenyl)-1,3-dihydro-imidazo[4,5-c]quinolin-2-one;
8-(2-Methoxy-pyrimidin-5-yl)-3-methyl-1-(4-[1,2,4]triazol-1-yl-3-trifluoromethyl-phenyl)-1,3-dihydro-imidazo[4,5-c]quinolin-2-one;
8-(2,4-Dimethoxy-pyrimidin-5-yl)-3-methyl-1-(4-[1,2,4]triazol-1-yl-3-trifluoromethyl-phenyl)-1,3-dihydro-imidazo[4,5-c]quinolin-2-one;
3-Methyl-1-(4-pyrazol-1-yl-3-trifluoromethyl-phenyl)-8-pyridin-3-yl-1,3-dihydro-imidazo[4,5-c]quinolin-2-one;
3-Methyl-1-(4-pyrazol-1-yl-3-trifluoromethyl-phenyl)-8-quinolin-3-yl-1,3-dihydro-imidazo[4,5-c]quinolin-2-one;
8-(6-Methoxy-pyridin-3-yl)-3-methyl-1-(4-pyrazol-1-yl-3-trifluoromethyl-phenyl)-1,3-dihydro-imidazo[4,5-c]quinolin-2-one;
8-(5-Methoxy-pyridin-3-yl)-3-methyl-1-(4-pyrazol-1-yl-3-trifluoromethyl-phenyl)-1,3-dihydro-imidazo[4,5-c]quinolin-2-one;
1-(3-Chloro-4-[1,2,4]triazol-1-yl-phenyl)-3-methyl-8-pyridin-3-yl-1,3-dihydro-imidazo[4,5-c]quinolin-2-one;
1-(3-Chloro-4-[1,2,4]triazol-1-yl-phenyl)-3-methyl-8-quinolin-3-yl-1,3-dihydro-imidazo[4,5-c]quinolin-2-one;
1-(4-Imidazol-1-yl-3-trifluoromethyl-phenyl)-3-methyl-8-pyridin-3-yl-1,3-dihydro-imidazo[4,5-c]quinolin-2-one;
1-(4-Imidazol-1-yl-3-trifluoromethyl-phenyl)-3-methyl-8-quinolin-3-yl-1,3-dihydro-imidazo[4,5-c]quinolin-2-one;
1-(4-Imidazol-1-yl-3-trifluoromethyl-phenyl)-8-(6-methoxy-pyridin-3-yl)-3-methyl-1,3-dihydro-imidazo[4,5-c]quinolin-2-one;
1-(4-Imidazol-1-yl-3-trifluoromethyl-phenyl)-8-(5-methoxy-pyridin-3-yl)-3-methyl-1,3-dihydro-imidazo[4,5-c]quinolin-2-one;
3-Methyl-8-pyridin-3-yl-1-(4-[1,2,4]triazol-1-ylmethyl-phenyl)-1,3-dihydro-imidazo[4,5-c]quinolin-2-one;
3-Methyl-8-quinolin-3-yl-1-(4-[1,2,4]triazol-1-ylmethyl-phenyl)-1,3-dihydro-imidazo[4,5-c]quinolin-2-one;
1-(4-Imidazol-1-ylmethyl-phenyl)-3-methyl-8-pyridin-3-yl-1,3-dihydro-imidazo[4,5-c]quinolin-2-one; and
1-(4-Imidazol-1-ylmethyl-phenyl)-3-methyl-8-quinolin-3-yl-1,3-dihydro-imidazo[4,5-c]quinolin-2-one;
or a tautomer thereof, or a pharmaceutically acceptable salt, or a hydrate or solvate thereof.

A very preferred compound of the present invention is 2-methyl-2-[4-(3-methyl-2-oxo-8-quinolin-3-yl-2,3-dihydro-imidazo[4,5-c]quinolin-1-yl)-phenyl]-propionitrile and its monotosylate salt. The synthesis of 2-methyl-2-[4-(3-methyl-2-oxo-8-quinolin-3-yl-2,3-dihydro-imidazo[4,5-c]quinolin-1-yl)-phenyl]-propionitrile is for instance described in WO2006/122806 as Example 1.

Another very preferred compound of the present invention is 8-(6-methoxy-pyridin-3-yl)-3-methyl-1-(4-piperazin-1-yl-3-trifluoromethyl-phenyl)-1,3-dihydro-imidazo[4,5-c]quinolin-2-one. The synthesis of 8-(6-methoxy-pyridin-3-yl)-3-methyl-1-(4-piperazin-1-yl-3-trifluoromethylphenyl)-1,3-dihydro-imidazo[4,5-c]quinolin-2-one is for instance described in WO2006/122806 as Example 86.

According to the present invention the treatment of the following symptoms with compounds of formula I is preferred:

Restenosis
Tuberous sclerosis
Lymphangioleiomyomatosis
Retinitis pigmentosis
Neurodegenerative disorders such as Parkinson's, Huntington's, Alzheimer's and dementias caused by tau mutations, spinocerebellar ataxia type 3, motor neuron disease caused by SOD1 mutations, neuronal ceroid lipofucinoses/Batten disease (pediatric neurodegeneration)
wet and dry macular degeneration
Neurofibromatosis including Neurofibromatosis type 1,
Peutz-Jeghers syndrome According to the present invention the treatment of Tuberous sclerosis or Peutz-Jeghers syndrome with compounds of formula I is especially preferred:

In particular, the present invention relates to a method of treating a mTOR kinase dependent disease comprising administering a therapeutically effective amount of a specific imidazoquinoline derivative of formula I, especially preferred 2-methyl-2-[4-(3-methyl-2-oxo-8-quinolin-3-yl-2,3-dihydro-imidazo[4,5-c]quinolin-1-yl)-phenyl]-propionitrile or 8-(6-methoxy-pyridin-3-yl)-3-methyl-1-(4-piperazin-1-yl-3-trifluoromethyl-phenyl)-1,3-dihydro-imidazo[4,5-c]quinolin-2-one, to a warm-blooded animal in need thereof.

Furthermore, the present invention relates to the use of a compound of formula I, especially preferred 2-methyl-2-[4-(3-methyl-2-oxo-8-quinolin-3-yl-2,3-dihydro-imidazo[4,5-c]quinolin-1-yl)-phenyl]-propionitrile or 8-(6-methoxy-pyridin-3-yl)-3-methyl-1-(4-piperazin-1-yl-3-trifluoromethyl-phenyl)-1,3-dihydro-imidazo[4,5-c]quinolin-2-one, for the manufacture of a pharmaceutical preparation for the treatment of a mTOR kinase dependent disease; a pharmaceutical preparation for the treatment of a mTOR kinase dependent disease comprising said compound or a pharmaceutically acceptable salt thereof and a pharmaceutically acceptable carrier; the use of said compound or pharmaceutically acceptable salt thereof for the treatment of a mTOR kinase dependent disease.

Treatment in accordance with the invention may be symptomatic or prophylactic.

A compound of the formula (I) may also be used for the treatment of mTOR kinase dependent diseases in combination with other active compounds for instance the combination partners as disclosed in WO2006/122806.

A compound of the formula (I) may also be used to advantage in combination with known therapeutic processes, for example, the administration of hormones or especially radiation. A compound of formula (I) may in particular be used as a radiosensitizer, especially for the treatment of tumors which exhibit poor sensitivity to radiotherapy.

By "combination" according to the invention, there is meant either a fixed combination in one dosage unit form, or a kit of parts for the combined administration where a compound of the formula (I) and a combination partner may be administered independently at the same time or separately within time intervals that especially allow that the combination partners show a cooperative, e.g. synergistic effect.

A compound of formula I can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds.

The dosage of the active ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The pharmaceutical compositions are comprising an amount effective in the treatment of one of the above-mentioned disorders, of a compound of formula I or an N-oxide or a tautomer thereof together with pharmaceutically acceptable carriers that are suitable for topical, enteral, for example oral or rectal, or parenteral administration and that may be inorganic or organic, solid or liquid. There are pharmaceutical compositions used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectioning, dissolving or lyophilising processes, and comprise approximately from 1% to 99%, especially from approximately 1% to approximately 20%, active ingredient(s).

The efficacy of the compounds of formula I and salts thereof as mTOR kinase inhibitors can be demonstrated as follows:

BIOCHEMICAL ASSAY

The K-LISA™ mTOR activity kit from Calbiochem (catalog CBA055) is used to evaluate 2-Methyl-2-[4-(3-methyl-2- oxo-8-quinolin-3-yl-2,3-dihydro-imidazo[4,5-c]quinolin-1-yl)-phenyl]-propionitrile (compound 1) and 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (compound 2). Compound 1, 2 or wortmannin are incubated with mTOR enzyme for 30 minutes on ice. This mixture is then transferred to a glutathione-coated 96-well plate pre-incubated with GST-S6K1 recombinant protein. Kinase reactions are initiated by adding kinase buffer containing 100 μM ATP and are incubated for 30 minutes at 30° C. mTOR activity is quantitated using an anti-phospho Thr389-HRP conjugate detection system. Wortmannin served as control compound for the mTOR kinase activity assay.

Methyl-2-[4-(3-methyl-2-oxo-8-quinolin-3-yl-2,3-dihydro-imidazo[4,5-c]quinolin-1-yl)-phenyl]-propionitrile (compound 1) inhibits mTOR kinase activity with mean $IC_{50}$-values of 20.7 nM. 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (compound 2) inhibits mTOR kinase activity with mean $IC_{50}$-values of 1.4 nM.

CELLULAR ASSAY

A 96-well "in-cell western" assay is used to quantitate the levels of ribosomal protein S6 phosphorylation following treatment of HeLa cells with compounds. HeLa cells are seeded on to 96-wells plates (5000 cells/well), cultured for 72 h prior to serum deprivation for 18 h, in a humidified environment of 5% $CO_2$ at 37° C. throughout. Thereafter, they are incubated in 200 μL of starve-medium for 180 min prior to a 60 min stimulation with 200 μL of test-medium. All solutions are pre-warmed for 30 min; the 96-well plates are sealed (Millipore) and incubated in a non-$CO_2$ incubator at 37° C. during the starvation and stimulation protocol. Cells are fixed by the addition of 50 μL of a 5× Mirsky's fixative solution for 60 min, before washing (8×200 μL TBS; Bio-Tek ELX405). After a 48 h blocking step in Tris buffered saline pH=7.2 containing 0.1% Triton-X100 and 0.1% bovine serum albumin, at 4° C., fixed cells are incubated overnight at 4° C. with the anti-phospho(Ser235-236)S6 primary antibody (Cell Signaling Technologies #2211 [can be substituted with Cell Signaling Technologies #2215 to quantitate S6 phosphorylation at Ser240-244]; 50 μL at 1:300 in blocking-solution), washed (8×200 μL TBS) before 100 μL of europium-labeled anti-rabbit secondary antibody (Perkin-Elmer; 2.4 μg/mL) is added for 90 min at room temperature in the dark. After a final wash (8×200 μL TBS), 100 μL of Delphia™ Enhancement-solution is added to each well and the fluorescence quantified 120 min later using an Envision 2101 (Perkin-Elmer).

Test medium contained 1× essential amino acids and 1 mM L-glutamine ("nutrients") in the presence or absence of 100 nM insulin.

2-Methyl-2-[4-(3-methyl-2-oxo-8-quinolin-3-yl-2,3-dihydro-imidazo[4,5-c]quinolin-1-yl)-phenyl]-propionitrile (compound 1) inhibits the induced phosphorylation of S6 with mean $IC_{50}$-values of 17 nM; 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (compound 2) inhibits the induced phosphorylation of S6 with mean $IC_{50}$-values of 11 nM,

The invention claimed is:

1. A method of inhibiting mammalian target of rapamycin (mTOR) kinase in a patient with mTOR kinase dependent disease comprising administering a therapeutically effective amount of a compound 2-methyl-2-[4-(3-methyl-2-oxo-8-quinolin-3-yl-2,3-dihydro-imidazo[4,5-c]quinolin-1-yl)-phenyl]-propionitrile, or a pharmaceutically acceptable salt thereof, to a patient in need thereof wherein said mTOR kinase dependent disease is selected from the group consisting of muscle wasting, atrophy and cachexia.

* * * * *